US00PP23837P3

(12) United States Plant Patent
Sheehan

(10) Patent No.: US PP23,837 P3
(45) Date of Patent: Aug. 20, 2013

(54) GRAPEVINE 'SHEEGENE-21'

(50) Latin Name: *Vitis vinifera*
Varietal Denomination: Sheegene-21

(75) Inventor: Timothy P. Sheehan, Vancouver, WA (US)

(73) Assignee: Sheehan Genetics, LLC, Fresno, CA (US)

( * ) Notice: Subject to any disclaimer, the term of this patent is extended or adjusted under 35 U.S.C. 154(b) by 0 days.

(21) Appl. No.: 13/373,861

(22) Filed: Dec. 2, 2011

(65) Prior Publication Data

US 2013/0145510 P1 Jun. 6, 2013

(51) Int. Cl.
*A01H 5/00* (2006.01)

(52) U.S. Cl.
USPC ..... Plt./207

(58) Field of Classification Search
USPC ..... Plt./207
See application file for complete search history.

*Primary Examiner* — Annette Para
(74) *Attorney, Agent, or Firm* — Baker Manock & Jensen, PC; Eric C. Cole, Esq.

(57) ABSTRACT

A new and distinct variety of grapevine characterized by the production of medium, green-colored seedless grapes that mature in early July, approximately four weeks earlier than 'Thompson Seedless' (unpatented) when grown in the San Joaquin Valley of Central California. The grapes of this new variety are produced on strong woody stems and branches and are well adapted to commercial handling.

1 Drawing Sheet

Latin name of the genius and species of the plant claimed: The claimed plant relates to a new and distinct variety of *Vitis vinifera* to be known as 'Sheegene-21'.

CROSS REFERENCE TO RELATED APPLICATIONS

The claimed plant is not subject of a related application.

STATEMENT OF ANY FEDERALLY-SPONSORED RESEARCH AND DEVELOPMENT

The claimed plant is not subject of Federally-sponsored research or development.

VARIETY DENOMINATION

The new variety of *Vitis vinifera* is the result of hybridization of 'Princess' (unpatented), the pollen parent, and 'Red Globe' (U.S. Plant Pat. No. 4,787), the seed parent. The new variety was asexually propagated by Timothy P. Sheehan in the Spring of 2000 in a *Vitis vinifera* variety block located near Fowler, Calif. The new variety was planted as rooted cuttings in May of 2007 in a field located north and west of Delano, Calif. The new variety produces a medium, green-colored seedless grape with very good flavor. The new variety has been shown to maintain its distinguishing characteristics through asexual propagation.

The new variety is distinguished from its pollen parent, 'Princess' (unpatented), in that the new variety produces green-colored seedless grapes, as compared to the white-colored seedless grapes produced by its pollen parent, 'Princess' (unpatented). The new variety is distinguished from its seed parent, 'Red Globe' (U.S. Plant Pat. No. 4,787), in that the new variety produces green-colored seedless grapes, as compared to its seed parent, 'Red Globe' (U.S. Plant Pat. No. 4,787), that produces red-colored seeded grapes.

BACKGROUND OF THE INVENTION

The present invention relates to a new and distinct variety of grapevine that produces a medium, green-colored seedless grape that matures during early July when grown in the San Joaquin Valley of Central California. The new invention resembles 'Thompson Seedless' (unpatented).

SUMMARY OF THE INVENTION

The 'Sheegene-21' grapevine is characterized by producing a medium, green-colored seedless grape that has very good flavor and it is productive and mature for harvesting and shipment in early July when grown in the San Joaquin Valley of Central California. The new variety can be compared to 'Thompson Seedless' (unpatented) but the grapes produced by the new variety mature approximately four weeks earlier, among other distinguishing characteristics.

BRIEF DESCRIPTION OF THE DRAWINGS

The accompanying drawing is a color photograph that displays a cluster of immature grapes and leaves along the top side, a cluster of mature grapes in the center, four grapes cut in half displaying the color of the flesh and the shape of the berries and three clusters of immature grapes in the lower center, a branch displaying the nodes along the left side, a shoot with mature and immature leaves with tendril along the right side, and on the bottom is a tendril with three leaves displaying the upper and lower leaf surface.

DETAILED BOTANICAL DESCRIPTION

Referring more to the horticultural description of the new and distinct variety of grapevine, the following has been observed under the ecological conditions prevailing at the origin vineyard located near Delano, Calif., in the San Joaquin Valley of Central California. All major color descriptions are by reference to the Dictionary of Color by Maerz & Paul, First Edition, published in 1930. Common colors names are also used in several instances.

Vine:
- *Size.*—Medium for three-year old vine.
- *Vigor.*—Very good.
- *Chilling requirements.*—Normal for grapevines in the lower San Joaquin Valley of Central California.
- *Regularity of bearing.*—Regular.

Trunk:
- *Size.*—Medium; 7 inches [17.78 cm] in circumference, 18 inches [45.72 cm] above ground.
- *Surface texture.*—Rough, shaggy.
- *Color of bark.*—Pl.4 F10 Near Ararby.
- *Mature cane color.*—Pl.5 D11 Mexico.
- *Nodes.*—Four nodes on each cane, 12 inches [30.48 cm] long.
- *Length between nodes.*—3¼ inches [8.26 cm].
- *Lenticel numbers.*—None.
- *Shoot length.*—1½ to 2¼ inches [3.81 to 5.72 cm].
- *Shoot shape.*—Droopy.
- *Tendrils number/location.*—Single at node.
- *Tendrils length.*—Medium; 2 inches [5.08 cm] on average.
- *Tendrils form.*—Bifurcate.
- *Tendrils texture.*—Firm.
- *Bud shape.*—Convex.
- *Bud size.*—0.19 to 0.20 inches [4 to 5 mm] in width, 0.25 to 0.30 inches [6 to 7 mm] in length.
- *Bud fruitfulness.*—Very good.

Branches:
- *Size.*—Medium; 2½ inches [6.35 cm] in circumference.
- *Cordons.*—21 inches from trunk (53.34 cm).
- *Surface texture.*—Slightly rough.
- *Color* (*one year or older branches*).—Pl.6 F4 Crushed Berry.
- *Color* (*immature branches*).—Pl.18 L8 Evergreen.

Leaves:
- *Size.*—Medium.
- *Density.*—Dense.
- *Average length.*—3 to 3¼ inches [7.62 to 8.26 cm].
- *Average width.*—3 to 5¼ inches [7.62 to 13.34 cm].
- *Form.*—Pentagonal.
- *Texture* (*upper surface*).—Smooth.
- *Texture* (*lower surface*).—Slightly rough.
- *Color* (*upward disposed surface*).—Pl.23 J9 Mt. Vernon gr.
- *Color* (*downward disposed surface*).—Pl.21 L7 Med. Dark gr.
- *Leaf vein color.*—Pl.17 L7 Viridine Y.
- *Marginal form.*—Toothed.
- *Leaf margin.*—Slightly undulating.
- *Leaf vein thickness.*—0.08 inches [2 mm].
- *Glandular characteristics.*—None.
- *Petiole size.*—Moderate.
- *Petiole length.*—1¾ to 2 inches [4.45 to 5.08 cm].
- *Petiole thickness.*—0.12 inches [3 mm].
- *Petiole color.*—Pl.6 J8 Domingo.
- *Petiole color* (*upper surface*).—Pl.16 L8 Dark Cardinal.
- *Petiole sinus form.*—Upside down 'U' shape.
- *Lobe* (*average*).—Four.
- *Tooth size.*—0.20 to 0.28 inches [5 to 7 mm] in width; 0.28 to 0.31 inches [7 to 8 mm] in length.
- *Tooth shape.*—Convex.

Inflorescence:
- *Size.*—4.33 to 7.48 inches [11 to 19 cm].
- *Number per spur.*—One to two.
- *Number per vine.*—Many; up to forty-two.
- *Quantity.*—Proficient.

Flowers:
- *Flower buds.*—0.04 to 0.08 inches [1 to 2 mm].
- *Flower buds surface.*—Glabrous.
- *Flower buds.*—Generally heavy.
- *Date of bloom.*—May 6.
- *Date of full bloom.*—May 11.
- *Size.*—0.20 inches [5 mm].
- *Petals* (*color*).—Pl.7 L8 Mauve Taupe.
- *Petals* (*size*).—Small; 0.18 inches [5 mm].
- *Pistil color.*—Pl.7 L8 Neva gr.
- *Date of visible berry set.*—May 11.
- *Size of berries.*—Small; 0.08 inches [ 2 mm].

Fruit:
- *Solids.*—18.0 Brix.
- *Acids.*—0.32.
- *Sugar/acid ratio.*—0.56.
- *Juice pH.*—3.85.
- *Seeds.*—None.
- *Capstem pedicel.*—0.24 to 0.39 inches [6 to 10 mm].
- *Berry weight.*—2.28 grams.
- *Juice color.*—Pl.19 B4 Corydalis gr.
- *Cluster size.*—Medium.
- *Cluster average length* (*not including stem*).—6.43 inches [16.33 cm].
- *Cluster average diameter.*—4.00 inches [10.26 cm].
- *Cluster average weight.*—12.5 oz. [356.25 grams].
- *Compactness.*—Compact.
- *Cluster form.*—Semi saucer-shaped.
- *Stem length.*—2.31 inches [5.87 cm].
- *Stem caliper.*—0.19 inches [0.47 cm].
- *Berry size.*—Medium.
- *Berry form.*—Ovate.
- *Berry numbers* (*average*).—156 berries per bunch.
- *Berry size* (*average dimension along longitudinal axis*).—1.00 inch [2.54 cm].
- *Berry size* (*average dimension along transverse axis*).—0.63 to 0.75 inches [15.8 to 19.1 mm].

Skin:
- *Skin thickness.*—Medium.
- *Texture.*—Semi-tough.
- *Ground color.*—Pl.19 B4; Corydalis gr.
- *Pulp.*—Pl.19 B4 Corydalis gr.
- *Lenticels.*—None.

Flesh:
- *Flesh color.*—Pl.19 B4 Corydalis gr.
- *Juice production.*—Moderate.
- *Flavor.*—Very good.
- *Aroma.*—Very mild.
- *Texture.*—Firm.
- *Ripening.*—Even.
- *Eating quality.*—Very good.
- *Use.*—Fresh Market.
- *Keeping quality.*—Good.
- *Resistance to disease.*—Unknown.
- *Harvesting.*—Late July in the San Joaquin Valley of Central California.
- *Shipping and handling qualities.*—Very good.

Having thus described and illustrated our new variety of grapevine, I claim:

1. A new variety of grapevine to be known as 'Sheegene-21' and parts thereof, substantially as illustrated and described, characterized principally by its production of medium, green-colored seedless grapes that mature earlier in the season of ripening than does 'Thompson Seedless' (unpatented) that is resembles.

* * * * *

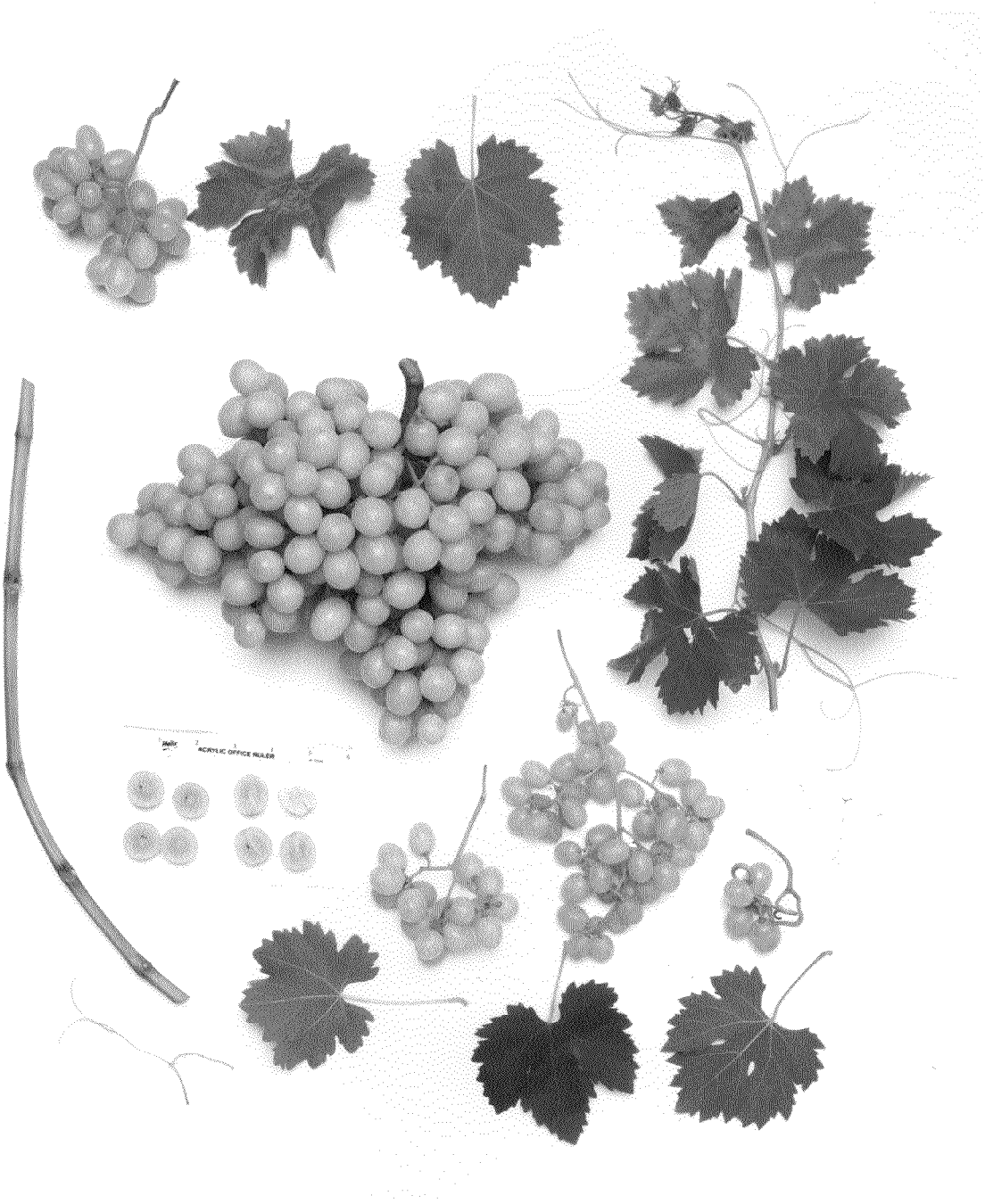
ACRYLIC OFFICE RULER